US009693551B2

(12) United States Patent
Liu et al.

(10) Patent No.: US 9,693,551 B2
(45) Date of Patent: Jul. 4, 2017

(54) PESTICIDAL DISPERSIBLE CONCENTRATE FORMULATIONS

(71) Applicant: Valent U.S.A., Corporation, Walnut Creek, CA (US)

(72) Inventors: Jane Liu, Pleasanton, CA (US); Toshiya Ogawa, San Ramon, CA (US); Christopher B. Meador, Leland, MS (US); Michael Seitz, Reno, NV (US); Dair McDuffee, Indianapolis, IN (US); Karen S. Arthur, Plano, TX (US)

(73) Assignee: VALENT U.S.A. CORPORATION, Walnut Creek, CA (US)

( * ) Notice: Subject to any disclaimer, the term of this patent is extended or adjusted under 35 U.S.C. 154(b) by 0 days.

(21) Appl. No.: 14/328,003

(22) Filed: Jul. 10, 2014

(65) Prior Publication Data

US 2015/0018402 A1 Jan. 15, 2015

Related U.S. Application Data

(60) Provisional application No. 61/845,620, filed on Jul. 12, 2013.

(51) Int. Cl.
*A01N 25/02* (2006.01)
*A01N 37/22* (2006.01)
*A01N 25/04* (2006.01)
*A01N 43/653* (2006.01)
*A01N 37/46* (2006.01)

(52) U.S. Cl.
CPC .............. *A01N 25/02* (2013.01); *A01N 25/04* (2013.01); *A01N 37/46* (2013.01); *A01N 43/653* (2013.01)

(58) Field of Classification Search
None
See application file for complete search history.

(56) References Cited

U.S. PATENT DOCUMENTS

| 2002/0193256 A1* | 12/2002 | Harris, Jr. ............. A01N 25/04 507/200 |
| 2009/0131462 A1* | 5/2009 | Gewehr ................. A01N 43/56 514/274 |
| 2011/0306643 A1 | 12/2011 | Vermeer et al. |
| 2012/0034315 A1* | 2/2012 | Hanagan ............. C07D 417/14 424/632 |
| 2012/0088665 A1* | 4/2012 | Dietz .................... A01N 37/50 504/100 |
| 2012/0208700 A1 | 8/2012 | Hopkins et al. |
| 2013/0137572 A1 | 5/2013 | Fowler et al. |
| 2013/0165487 A1 | 6/2013 | Arthur et al. |

FOREIGN PATENT DOCUMENTS

WO WO-2007-110355 * 10/2007

OTHER PUBLICATIONS

Carareto et al., "Water Activity of Aqueous Solutions of Ethylene Oxide-Propylene Oxide Block Copolymers and Maltodextrins", Brazilian Journal of Chemical Engineering, vol. 27, p. 173-181, Jan.-Mar. 2010.*
International Search Report and Written Opinion issued by the International Bureau on Oct. 30, 2014.

* cited by examiner

*Primary Examiner* — Jianfeng Song
(74) *Attorney, Agent, or Firm* — Wood, Phillips, Katz, Clark & Mortimer

(57) ABSTRACT

The present invention relates to non-aqueous pesticidal dispersible concentrate formulations comprising from about 2 to about 10% of at least one pesticidal agent, from about 15 to about 25% of hexylene glycol, from about 65 to about 75% of propylene glycol, a hydrophobic silica, and a surfactant, wherein the weight percentages are based on the total weight of the formulation. Formulations of the present invention have superior storage stability but are non-phytotoxic to seeds when used as a seed treatment. The present invention also relates to ready-to-use products made from the concentrated formulations of the present invention. Further, the present invention includes methods of using the pesticidal dispersible concentrate formulations and ready-to-use products to achieve superior plant protection and disease control.

9 Claims, No Drawings

PESTICIDAL DISPERSIBLE CONCENTRATE FORMULATIONS

FIELD OF THE INVENTION

The present invention relates generally to concentrated dispersible formulations that protect plant propagation materials against attack by pests, ready-to-use products prepared from the concentrated formulations, and methods of using the formulations to protect plant propagation material from pests.

BACKGROUND OF THE INVENTION

The practice of treating seeds or other plant propagation material with pesticide formulations is well known. The pesticide formulation should not harm the seeds, be stable for relatively long periods of time before planting, adhere well and evenly to the seeds, be compatible with planting equipment, and be relatively inexpensive.

Insecticides and fungicides are applied to seeds to protect them from pests throughout their life cycle, but seed treatments are especially effective for protecting the plants from pests prior to and during germination, and in the seedling stage. Seed treatment formulations can be dusts, slurries or liquids. Two common liquid seed treatment formulations are dispersible concentrates and flowable concentrates for seed treatments.

A variety of pesticidal agents are insoluble or not readily soluble in water. To overcome this problem, seeds can be treated with formulations such as wettable powders, dry flowables, emulsifiable concentrates and other similar single-phase formulations that are mixed with water by the user prior to application. These types of formulations have several disadvantages including dusting during handling (possibly causing injury to the user and the nearby environment), inhomogeneous mixing by the user (resulting in uneven pesticide distribution), and settlement or clogging of spray tank screens during application. These formulations also have the disadvantage of requiring agitation or further mixing during application. Further, these formulations may require milling which can significantly increase manufacturing costs.

A dispersible concentrate (DC) is a liquid formulation that is applied as a solid dispersion after dilution in water. A water miscible organic fluid, or a mixture of multiple fluids, is usually used to dissolve water-insoluble or partially soluble pesticidal agents. After dilution in water, the pesticidal agents precipitate out and disperse as micronized solid particles as the carrier fluid is dissolved in water. Dispersible concentrates contain surfactants that make a uniform and stable dispersion of the precipitated solid particles. The formulation may include water as long as the liquid mixture maintains sufficient solubility of the pesticidal agents in it. Furthermore, DC formulations may contain other ingredients that function in various ways either in the formulation itself or when it is diluted with water, or when the product is applied on to seeds or other plant propagation materials. These ingredients include compatibility agents, stickers, film formers, slip agents, colorants, etc. These additives may not be dissolved but dispersed in the carrier liquid; therefore, the DC may not always look homogeneous. By choosing the appropriate organic fluids, the pesticidal active ingredients can remain physically and chemically stable for an extended period of time, ensuring a long shelf life for the product.

It is known that stable aqueous suspension concentrate formulations are not easily obtained for certain pesticidal agents that have relatively higher water solubility and/or lower melting point. For example, metalaxyl (mp 63-72° C. for the technical grade, water solubility 8400 ppm) is one such compound. Obtaining stable aqueous suspension formulations of metalaxyl is very challenging because it is difficult to prevent the compound from re-crystallizing and causing physical instability during storage.

Besides the storage concerns, dispersible concentrates typically cannot be used as a seed treatment. Conventional dispersible concentrates contain solvents that reduce the germination rate of the seeds and therefore are not desirable for application to seeds.

Further, obtaining stable formulations that are safe for seeds and effective requires the formulator to decide on the presence or absence of many inert additives. There are hundreds of options for some types of additives. The art of creating formulations with the desired characteristics by picking the precise components and their precise amounts is unpredictable. Often slight changes in amounts or substitutions of additives result in a formulations with entirely different characteristics that one skilled in the art would expect. Extensive experimentation is sometimes needed to prepare desirable formulations. Formulating pesticides for seed treatments involves knowledge of the thermodynamics of mixing, phase equilibria, solutions, surface chemistry, colloids, emulsions and suspensions, among other things.

Fungal infections are a major concern for crop growers. Fungi can be present on the seed surface prior to planting, they can be soil-borne, or they can be introduced into the growing environment by mobile pests or equipment. Fungi infect seeds and seedlings and destroy plant cells and tissues and thereby prevent seed germination or cause poor development or death of seedlings. *Aphanomyces, Fusarium, Helminthosporium, Pythium*, and *Rhizoctonia* are all known to cause infection and death of plants. These organisms cause seed rot, damping-off, seed blight, and root rot. Diseases that affect adult plants can also be controlled by pesticidal seed treatments (e.g., smuts caused by *Ustilago, Tilletia*, and *Urocystis*).

There remains a need in the art for a dispersible concentrate formulation that readily dissolves the pesticidal agent, maintains physical and chemical stability during long-term storage under environmentally stressful conditions, and exhibits excellent seed protection. There also remains a need in the art for a dispersible concentrate formulation that readily mixes with flowable concentrates for seed coatings. Furthermore, there is a need in the art for a dispersible concentrate that is easily diluted by an end user to prepare a seed treatment that provides improved protection against fungal pests.

SUMMARY OF THE INVENTION

Applicants discovered that a combination of specific solvents in a dispersible concentrate resulted in a plant safe, pesticidally effective, highly concentrated formulation with excellent storage stability.

Specifically, in one aspect, the present invention is directed to non-aqueous pesticidal dispersible concentrate formulations that include from about 2 to about 10% of at least one pesticidal agent, from about 15 to about 25% of hexylene glycol, from about 65 to about 75% of propylene glycol, a hydrophobic silica, and a surfactant, wherein the weight percentages are based on the total weight of the formulation.

In another aspect, the present invention is directed to non-aqueous pesticidal dispersible concentrate formulations that include from about 2 to about 3% of metconazole, from about 4 to about 5% of metalaxyl, from about 19 to about 21% of hexylene glycol, from about 69 to about 71% of propylene glycol, from about 1 to about 2% of a fumed hydrophobic silica after treatment with hexamethyl disilazane, and from about 1 to about 2% of a difunctional block copolymer surfactant, wherein the weight percentages are based on the total weight of the formulation.

In yet another aspect of the invention, the formulation is a non-aqueous pesticidal dispersible concentrate that includes about 2.3% metconazole, about 4.5% metalaxyl, about 20% hexylene glycol, about 70.1% propylene glycol, about 1.5% fumed hydrophobic silica after treatment with hexamethyl disilazane, and about 1.5% of a difunctional block copolymer surfactant with terminal primary hydroxyl groups.

In another aspect, the invention is directed to ready-to-use products prepared by diluting the formulations of the present invention.

In a further aspect, the invention is directed to methods of protecting plants which include the step of treating plant propagation materials with a fungicidally effective amount of the ready-to-use product based on formulations of the present invention.

In a final aspect, the invention is directed to methods of protecting plant propagation material from pests that include the step of treating the plant propagation material with an effective amount of the formulations of the present invention.

DETAILED DESCRIPTION OF THE INVENTION

The present invention relates to pesticidal dispersible concentrate formulations comprising at least one pesticidal agent and a solvent selected from the group consisting of alkyl diols, alkyl triols and a mixture thereof.

Applicants discovered that the use of alkyl diols and/or alkyl triols as solvents for pesticidal agents in dispersible concentrates unexpectedly results in a safe and stable product that can effectively control target diseases. Dispersible concentrates of the present invention do not form crystals even when stored at −18° C. for one and a half years. Further, dispersible concentrates of the present invention were chemically and physically stable at elevated temperatures and after freeze-thaw cycles.

In one embodiment the invention is directed to non-aqueous pesticidal dispersible concentrate formulations comprising from about 2 to about 10% of at least one pesticidal agent, from about 15 to about 25% of hexylene glycol, from about 65 to about 75% of propylene glycol, a hydrophobic silica, and a surfactant, wherein the weight percentages are based on the total weight of the formulation.

In another embodiment, the at least one pesticide is a fungicide. In a preferred embodiment, the formulation contains the fungicides metconazole and metalaxyl.

In an embodiment, the surfactant is a difunctional block copolymer. In a preferred embodiment, the difunctional block copolymer surfactant has terminal primary hydroxyl groups, such as Pluronic® P 104 (Pluronic is a registered trademark of BASF).

In yet another embodiment, the formulation's hydrophobic silica is a fumed hydrophobic silica that has been treated with hexamethyl disilazane.

In a further embodiment, the invention is directed to non-aqueous pesticidal dispersible concentrate formulations comprising from about 6 to about 8% of at least one pesticidal agent, from about 18 to about 22% of hexylene glycol, from about 68 to about 72% of propylene glycol, from about 1 to about 2% of hydrophobic silica, and from about 1 to about 2% of a surfactant, wherein the weight percentages are based on the total weight of the formulation.

In another embodiment, the invention is directed to non-aqueous pesticidal dispersible concentrate formulations comprising from about 6 to about 7% of at least one pesticidal agent, from about 19 to about 21% of hexylene glycol, from about 69 to about 71% of propylene glycol, from about 1 to about 2% of a fumed hydrophobic silica that has been treated with hexamethyl disilazane, and from about 1 to about 2% of a difunctional block copolymer surfactant, wherein the weight percentages are based on the total weight of the formulation. In a preferred embodiment, the pesticidal agent is from about 2 to about 3% of metconazole and from about 4 to about 5% of metalaxyl. Most preferably, the pesticidal agent is about 2.3% metconazole and about 4.5% metalaxyl.

In a preferred embodiment, the formulation contains the most preferred amount of the fungicides, about 2.3% metconazole and about 4.5% metalaxyl and about 20% hexylene glycol, about 70.1% propylene glycol, about 1.5% fumed hydrophobic silica that has been treated with hexamethyl disilazane, and about 1.5% of a difunctional block copolymer surfactant with terminal primary hydroxyl groups, wherein the weight percentages are based on the total weight of the formulation.

In an alternative embodiment, the invention is directed to a ready-to-use product prepared from the formulations of the present invention. Preferably, this ready-to-use product contains from about 0.1 to about 5% of at least one pesticidal agent, from about 1 to about 16% of hexylene glycol, from about 5 to about 55% of propylene glycol, from about 0.1 to about 1.2% of hydrophobic silica, from about 0.1 to about 10% surfactant, and from about 5 to about 99% water, wherein the weight percentages are based on the total weight of the formulation.

In an embodiment, the invention is directed to methods of protecting plants that include the step of treating plant propagation materials with a fungicidally effective amount of the ready-to-use products of the present invention.

In a final embodiment, the invention is directed to methods of protecting plant propagation materials from pests comprising applying to the plant propagation materials an effective amount of the formulations of the present invention.

The disclosed embodiments are simply exemplary embodiments of the inventive concepts disclosed herein and should not be considered as limiting, unless the claims expressly state otherwise.

Pesticidal agents that can be used in formulations of the present invention include, but are not limited to, acaricides, avicides, bactericides, fungicides, herbicides, insecticides, miticides, molluscicide, nematicides, piscicides, rotenticides, and silivicdes.

Insecticides that can be used in the formulations of the present invention include, but are not limited to: neonicotinoid insecticides like clothianidin, imidacloprid, thiamethoxam, acetamiprid, and thiacloprid; antibiotic insecticides like abamectin, emamectin benzoate, and spinosyns A and B; carbamate insecticides like bendiocarb, carbaryl, carbofuran, pirimicarb, isoprocarb, methiocarb, thiodicarb; pyrethroid insecticides like acrinathrin, deltamethrin; phenylpyrazole insecticides like ethiprole, fipronil; organochlorine insecticides like endosulfan; organophosphorus insecticides like coumaphos; diamide insecticides like chlorantraniliprole, flubendiamide; benzoylurea insecticides like bistrifluoron, chlofluazuron, diflubenzuron, flucycloxuron, hexaflumuron, novaluron, teflubenzuron, triflumuron; insect growth regulators like buprofezin; and similar classes of insecticides.

Examples of fungicides that can be used in the formulations of the present invention include, but are not limited to: antibiotic fungicides like antimycin A1; strobilurin fungicides like azoxystrobin, dimoxystrobin, fluoxastrobin, kresoxim-methyl; carbamate fungicides like benthiavalicarb-isopropyl, carbendazim, diethofencarb, iprovalicarb, thiophanate-methyl; dicarboximide fungicides like captafol, captan, famoxadone, folpet, iprodione, procymidone, vinclozolin; triazole fungicides like bitertanol, bromuconazole, cyproconazole, diclobutrazol, difenoconazole, diniconazole, epoxiconazole, fenbuconazole, fluquinconazole, flutriafol, hexaconazole, imibenconazole, ipconazole, metconazole, prothioconazole, simeconazole, tebuconazole, triadimefon, triadimenol, triticonazole; amide fungicides like boscalid, carboxin, carpropamid, dicyclomet, ethaboxam, fenfuram, fenhexamid, flusulfamide, flutolanil, furametpyr, mepronil, ofurace, oxadixyl, pyracarbolid, thifluzamide, tiadinil, zoxamide; aromatic fungicides like chloroneb, chlorothalonil; imidazole fungicides like cyazofamid, fenamidone, triazoxide; the aliphatic nitrogen fungicides like cymoxanil; morpholine fungicides like dimethomorph; pyrimidine fungicides like fenarimolferimzone, mepanipyrim, nuarimol, pyrimethanil; pyrrole fungicides like fenpiclonil, fludioxonil; pyridine fungicides like fluazinam, fluopicolide; benzimidazole fungicides like fuberidazole, thiabendazole; dithiocarbamate fungicides like mancozeb, maneb, thiram, ziram; quinoline fungicides like quinoxyfen; aromatic fungicides like quintozene; miscellaneous (unclassified) fungicides like diclomezine, dithianon, pencycuron, pyroquilon, tricylazole; 2-[2-(2,5-dimethylphenoxymethyl)phenyl]-2-methoxy-N-methylacetamide; aromatic hydrocarbon:chlorophenyl fungicides like tolclofos-methyl; phenylamide: acylalanine fungicides like metalaxyl (available from Nufarm Ltd. or LG Life Sciences, Ltd.), metalaxyl-M, benalaxyl, benalaxyl-M, and furalaxyl-M; and related types of fungicides. In a preferred embodiment, the pesticidal agents are solids with a melting point above 65 and more preferably from about 68 to about 72 degrees Celsius. In a preferred embodiment, the melting point is about 70 degrees Celsius.

As previously mentioned, stable formulations containing metalaxyl are difficult to obtain because metalaxyl forms undesirable crystals. Applicants unexpectedly found that formulations of the present invention provide a superior solution to this known problem in the art.

The terms "insecticides" and "fungicides" are used broadly and are intended to cover all compounds active against insects and fungi. The compounds may belong to a wide range of compound classes. The pesticidal agents used in a formulation made in accordance with this invention may be a combination of the insecticides and fungicides selected to control a number of pests, insects and/or fungi, through the use of one formulation. Furthermore, it is anticipated that a formulation made in accordance with this invention may also contain auxiliary pesticidal agents that do not conform to the requirements set forth in this invention, provided that these auxiliary pesticidal agents are compatible with said formulation as determined by compatibility tests well known by those familiar with the art. For example, water-soluble pesticidal agents may be dissolved in the water carrier used in a flowable concentrate for seed treatment and mixed with formulations of the present invention prior to application to the seeds without affecting the suspension of the primary, solid pesticidal agents that are the subject of this invention. Another example of an auxiliary pesticidal agent is an encapsulated pesticidal agent, wherein a water-insoluble liquid or low melting insecticide and/or fungicide is enveloped by a solid shell or encased in a solid matrix, and then added to a formulation described in this invention.

Formulations of the present invention include alkyl diols and/or alkyl triols as a solvent. Examples of alkyl diols include, but are not limited to, butylene glycol, pentanediol, hexylene glycol, octylene glycol, decylenediol, dodecylenediol and propylene glycol. In a preferred embodiment the alkyl diols are hexylene glycol and propylene glycol. Examples of alkyl triols include, but are not limited to, glycerol, butane triols, trimethylolpropane, trimethylolethane, and hexane triol.

Hydrophobic silicas that can be used in accordance with the present invention include, but are not limited to, Aerosil® R 972 (Aerosil is a registered trademark of Evonik Degussa GMBH), Aerosil R 974 and Aerosil® R 812. Applicants unexpectedly found that adding hydrophobic silicas to formulations of the present invention allowed for improved mixing with flowable concentrates for seed treatments. Furthermore, Applicants have discovered that the addition of hydrophobic silica to the dispersible concentrate formulations allows blending with suspension concentrates for an extended period of time without causing significant phase separation. The addition of silica allows for formulations of the present invention to be mixed with flowable concentrates in blended products for several months prior to application to the seeds without significant separation or sedimentation of the pesticides.

Formulations of the present invention can also contain plant growth regulators. Plant growth regulators that can be used in accordance with the present invention include, but are not limited to, p-Chlorophenoxyacetic acid (4-CPA), Indole-3-acetic acid Free acid (IAA), alpha-Naphthaleneacetic acid Free acid (NAA), beta-Naphthoxyacetic acid Free acid (NOA), Phenylacetic acid (PAA), Picloram, 2,4,5-Trichlorophenoxyacetic acid, 6-Benzylaminopurine (BA), N-Benzyl-9-(2-tetrahydropyranyl) adenine (BPA), N-(2-Chloro-4-pyridyl)N'-phenylurea (4-CPPU), 6-(gamma, gamma-Dimethylallylamino)purine (2iP), 1,3-Diphenylurea (DPU), Kinetin, 1-Phenyl-3-(1,2,3-thiadiazol-5-yl) urea, (±)-cis,trans-Abscisic acid (S-ABA), Ancymidol, Chlorocholine chloride (CCC, chlormequat chloride+choline chloride (5C chlormequat), 3,6-Dichloro-o-anisic acid (Dicamba), Gibberellic acid (GA3), Gibberellin (GA4), (±)-jasmonic acid, Phloroglucinol, N-(Phosphonomethyl) glycine (Glyphosate), Succinic acid 2,2-dimethylhydrazide, and trinexapac-ethyl and salts and acids thereof.

Polyvinyl alcohols that can be added to formulations of the present invention include, but are not limited to, Selvol® 24-203 (Selvol is a registered trademark of Sekisui Specialty Chemicals America, LLC), Selvol® 205, Selvol® 502, Selvol® 513, Selvol® 518, Selvol® 523, Selvol® 103, Selvol® 305, Selvol® 310, Selvol® 325, Selvol® 418, Selvol® 425, and Erkol V 03/240.

Vinyl acetate/vinyl pyrrolidone copolymers that can be added to the formulations of the present invention include, but are not limited to, Agrimer® VA 6 (Agrimer is a registered trademark of ISP Investment, Inc.).

Graft copolymers that can be added to the formulations of the present invention include, but are not limited to, copolymers with an acrylic acid, acrylate, methacrylate, or methyl methacrylate backbone. From the backbone, various segments, for example, polyethylene glycol segments, may extend. In a preferred embodiment, graft copolymers are comb-branched, hydrophilic polymers with a backbone of acrylic acid, acrylate, methacrylate, or methyl methacrylate with polyethylene glycol (PEG) branches extending from this backbone. Suitable graft copolymers include, but are not limited to Tersperse® 2500 (a 35% graft copolymer solution; Tersperse is a registered trademark of Huntsman Petrochemical), Atlox® 4913 (a 35% graft copolymer; Atlox is a registered trademark of Uniqema Americas LLC), Ethacryl® P (a 35-45% graft copolymer solution; Ethacryl is a registered trademark of Coatex SAS), and the like.

Wetting agents that can be added to the formulations of the present invention include, but are not limited to: polyarylalkoxylated phosphate esters and their potassium salts (e.g., Soprophor® FLK; Soprophor is a registered trademark of RhodiaChimie, Stepfac TSP PE-K made by Stepan Corp., etc). Other suitable wetting agents include sodium dioctylsulfosuccinates (e.g., Geropon® SDS; Geropon is a registered trademark of RhodiaChimie, Aerosol® OT; Aerosol is a registered trademark of Cytec Technology), and ethoxylated alcohols (e.g., Trideth-6; Rhodasurf® BC 610; Rhodasurf is a registered trademark of RhodiaChimie; Tersperse® 4894).

Nonionic surfactants that can be used in accordance with the present invention include, but are not limited to, alkoxylated triglycerides, alkoxylated fatty alcohols, alkoxylatedtristyryl phenols, ethoxylated fatty acids, alkyl polyglycosides, fatty acid PEG esters, alkoxylatedsorbitan esters, polyoxyethylenepolyoxypropylene block polymers, polyoxyethylenepolyoxypropylene alkyl aryl ethers, polyoxyethylenepolyoxypropylene alkyl ethers, polyoxyethylenepolyoxypropylenepolyaryl ethers, polyoxyethylene fatty acid esters, and fatty acid esters of polyoxyethylenepolyoxypropylene block polymers. As mentioned above, Pluronic® P 104 is a preferred surfactant.

The present invention can include preservatives. Preservatives that can be used in accordance with the present invention include, but are not limited to, a 5-chloro-2-methyl-4-isothiazolin-3-one and 2-methyl-4-isothiazolin-3-one solution in water, such as Kathon® CG/ICP (Kathon is a registered trademark of Rohm and Haas Company), Proxel® GXL (Proxel is a registered trademark of Arch UK Biocides Limited) and Legend MK® (Legend MK is a registered trademark of Rohm and Haas Company).

The invention further relates to a method of applying the formulations to seeds. Techniques of seed treatment application are well known to those skilled in the art, and they may be used readily in the context of the present invention. Seed application methods include film coating, encapsulation, soaks/immersion, or any technique that is known by one of skill in the art.

Formulations of the present invention are especially suited for application to seeds and plant propagation material. The terms "plant propagation material" and "seeds" are used interchangeably throughout the specification. These terms are to be understood to denote all the generative parts of the plant such as seeds and vegetative plant material (i.e. cuttings and tubers, roots, bulbs, rhizomes, and shoots) that can be used for the multiplication of plants. Preferably, the treatment of plant propagation materials with a formulation of the present invention is used for controlling a multitude of fungi on cereals, such as wheat, rye, barley and oats, rice, corn, cotton and soybeans.

The phrase "effective amount" of the formulation means a sufficient amount of the formulation to provide the desired effect. In general, the formulation is employed in amounts that do not inhibit germination of the seeds (or cause phytotoxic damage to the seeds) while providing adequate pest control. Pest control can mean reducing pest damage to the plant, reducing the amount of pests on the plant or in its immediate environment, or preventing the pests from reproducing, among other things. The amount of the formulation may vary depending on specific crops and other factors. It is well within the ordinary skill in the art to determine the necessary amount of the formulation. For example, for corn, wheat or barley, the formulations of the present invention could be applied at the rate of from about 0.2 to about 5 fluid ounces per hundred weight of seed (fl oz/cwt), preferably from about 0.05 to about 3, and most preferably at about 1 fluid oz/cwt.

The formulations of the present invention can be applied to any environment in need of pest control. The environment in need of pest control may include any area that is desired to have a reduced number of pests or to be free of pests. For example, the pesticide can be applied to areas where crop plants are grown.

Dispersible concentrate formulations of the present invention do not necessarily contain water, or if they do, the amounts of water are relatively smaller than in all-in-one formulations. Because water is added by the end user to achieve the proper concentration, the initial concentration of the active ingredients in dispersible concentrates must be higher than in all-in-one formulations (which typically contain higher amounts of water than dispersible concentrates).

As used herein, all numerical values relating to amounts, weight percentages and the like, are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The following examples are intended to illustrate the present invention and to teach one of ordinary skill in the art how to make and use the invention. They are not intended to be limiting in any way.

EXAMPLES

Example 1

Preparation of a Dispersible Concentrate Formulation

Applicants prepared a concentrated dispersible formulation containing metconazole and metalaxyl as follows. An 8% dispersion of Aerosil® R 812 in propylene glycol was prepared by slowly adding 15 grams of Aerosil® R 812 into 172.5 grams of propylene glycol, under high-shear agitation. A solution of metconazole and metalaxyl was prepared by dissolving 22.9 grams of metconazole and 45.8 grams of metalaxyl into a mixture of 200 grams of hexylene glycol and 500 grams of propylene glycol under agitation and heating. Then 15 grams of Pluronic® P-104 was added to the solution and dissolved. After the fungicide actives and the surfactant were completely dissolved, the 187.5 grams of the 8% Aerosil dispersion and the remaining 28.8 grams of propylene glycol were added and blended until a homogeneous formulation (1,000 grams) was obtained.

Metconazole technical powder (approximately 99% purity) was used as the source of metconazole. Metalaxyl technical powder (approximately 98% purity) was used as the source of metalaxyl.

TABLE 1

Formulation of Example 1

| Component/Role in Formulation | % w/w |
|---|---|
| Metconazole Technical/Active | 2.29 |
| Metalaxyl Technical/Active | 4.58 |
| Hexylene Glycol/Solvent | 20 |
| Pluronic ® P 104/Surfactant | 1.5 |
| Aerosil ® R 812/Silica wetting agent | 1.5 |
| Propylene Glycol/Solvent | 70.1 |

Applicants therefore prepared a dispersible concentrate formulation comprising about 2.3% metconazole and about 4.5% metalaxyl ("Formulation of Example 1").

Example 2

Storage Stability Testing

The formulations of the present invention were subjected to seed safety and efficacy testing as indicated below.

TABLE 2

Chemical Stability

| | Initial | F/T (−10° C./ 40° C.) 5 cycles | 50° C./ 4 weeks | 50° C./ 8 weeks | 40° C./ 8 weeks | 40° C./ 16 weeks |
|---|---|---|---|---|---|---|
| % a.i. of metconazole | 2.3 | 2.3 | 2.3 | 2.3 | 2.3 | 2.3 |
| % a.i. of metalaxyl | 4.5 | 4.5 | 4.5 | 4.5 | 4.5 | 4.5 |

The Chemical Stability study showed that the active ingredients remained stable and did not break down.

TABLE 3

Physical Stability

| | | Initial | F/T (−10° C./40° C.) 5 cycles | 50° C./ 4 weeks | 50° C./ 8 weeks | 40° C./ 8 weeks | 40° C./ 16 weeks |
|---|---|---|---|---|---|---|---|
| Appearance | | No crystal | No crystal | No crystal | No crystal | No crystal | No crystal |
| pH (5% dilution in water) | | 4.6 | 4.6 | 4.5 | 4.6 | 4.7 | 4.8 |
| Dispersibility (1 hour) 10 ml sample/90 ml water | In 34 ppm hard water | No separation | No separation | No separation | Trace crystal at bottom | Trace crystal at bottom | Trace crystal at bottom |
| | In 1000 ppm hard water | No separation | No separation | No separation | Trace crystal at bottom | Trace crystal at bottom | Trace crystal at bottom |

Applicants unexpectedly found that the Formulation of Example 1 had excellent storage stability. The active ingredients did not form crystals or settle out of the formulation when stored for a long period of time and/or under environmentally stressful conditions. Applicants were surprised that metalaxyl did not settle out of the formulation because this is known problem in the art. The formulation produced only very small amounts of crystals when diluted.

Example 3

Ready-to-Use Products from the Formulation of Example 1

Applicants prepared products that were ready to be used on seeds. Applicants blended the Formulation of Example 1 with NipsIt INSIDE Insecticide (a clothianidin containing pesticide) at four different ratios (1:0.25, 1:0.5, 1:1 and 1:1.79), and diluted with water and red colorant to the required concentrations. The tank mix blends were chemically and physically stable when stored for seven days at a room temperature. There were changes in the pH and in the median particle size, which increased due to some crystal formation in the dilution. However, the crystals found were small; there was no residue found on 100 mesh screen. The micro-crystalline settling on the bottom was not hard packed and was easily resuspendible.

TABLE 4

| Product name | Active | % a.i. | Blend ratio (vol) | Blend by % wt |
|---|---|---|---|---|
| NipsIt INSIDE | clothianidin | 47.8 | 0.25 | 2.8 |
| Form. of Ex. 1 | Metalaxyl/ Metconozole | 4.5/2.2 | 1 | 9.2 |
| Red Coat | Red Colorant | | 0.3 | 3.12 |
| Tap Water | Water | 100 | 9.45 | 84.8 |
| | Total | | 11.00 | 100.0 |

TABLE 5

| Product name | Active | % a.i. | Blend ratio (vol) | Blend by % wt |
|---|---|---|---|---|
| Nipsit INSIDE | clothianidin | 47.8 | 0.5 | 5.6 |
| Form. of Ex. 1 | Metalaxyl/ Metconozole | 4.5/2.2 | 1 | 9.2 |
| Red Coat | Red Colorant | | 0.3 | 3.1 |
| Tap Water | Water | 100 | 9.2 | 82.1 |
| | Total | | 11.00 | 100.0 |

TABLE 6

| Product name | Active | % a.i. | Blend ratio (vol) | Blend by % wt |
|---|---|---|---|---|
| Nipsit INSIDE | clothianidin | 47.8 | 1 | 11.1 |
| Form. of Ex. 1 | Metalaxyl/ Metconozole | 4.5/2.2 | 1 | 9.1 |
| Red Coat | Red Colorant | | 0.3 | 3.1 |
| Tap Water | Water | 100 | 8.7 | 76.8 |
| | Total | | 11.00 | 100.0 |

TABLE 7

| Product name | Active | % a.i. | Blend ratio (vol) | Blend by % wt |
|---|---|---|---|---|
| Nipsit INSIDE | clothianidin | 47.8 | 1.79 | 19.5 |
| Form. of Ex. 1 | Metalaxyl/Metconozole | 4.5/2.3 | 1.0 | 8.9 |
| Red Coat | Red Colorant |  | 0.3 | 3.0 |
| Tap Water | Water | 100 | 7.91 | 68.5 |
| Total |  |  | 11.00 | 100.0 |

TABLE 8

Chemical and Physical Stability (Treat 1)
1312-25-1

|  |  | Storage days |  |  |  |
|---|---|---|---|---|---|
|  |  | Initial | 1 | 2 | 7 |
| % ai | Clothianidin | 1.46 |  | 1.47 | 1.47 |
|  | Metconazole | 0.222 |  | 0.221 | 0.220 |
|  | Metalaxyl | 0.424 |  | 0.425 | 0.425 |
|  | pH | 7.9 | 8.0 | 8.1 | 7.7 |
| residue on 100 mesh sieve (%) |  | 0.003 |  |  | 0.000 |
| Median particle size (µm) |  | 0.17 | 0.98 | 1.07 | 0.99 |

TABLE 9

Chemical and Physical Stability (Treat 2)
1312-25-2

|  |  | Storage days |  |  |  |
|---|---|---|---|---|---|
|  |  | Initial | 1 | 2 | 7 |
| % ai | Clothianidin | 2.85 |  | 2.86 | 2.82 |
|  | Metconazole | 0.218 |  | 0.219 | 0.215 |
|  | Metalaxyl | 0.424 |  | 0.423 | 0.417 |
|  | pH | 7.9 | 8.0 | 8.1 | 7.8 |
| residue on 100 mesh sieve (%) |  | 0.003 |  |  | 0.000 |
| Median particle size (µm) |  | 0.17 | 0.75 | 0.22 | 1.26 |

TABLE 10

Chemical and Physical Stability (Treat 3)
1312-25-3

|  |  | Storage days |  |  |  |
|---|---|---|---|---|---|
|  |  | Initial | 1 | 2 | 7 |
| % ai | Clothianidin | 5.45 |  | 5.46 | 5.46 |
|  | Metconazole | 0.210 |  | 0.211 | 0.209 |
|  | Metalaxyl | 0.411 |  | 0.411 | 0.410 |
|  | pH | 7.9 | 7.9 | 8.0 | 7.4 |
| residue on 100 mesh sieve (%) |  | 0.002 |  |  | 0.000 |
| Median particle size (µm) |  | 0.20 | 0.23 | 0.25 | 1.13 |

TABLE 11

Chemical and Physical Stability (Treat 4)
1312-25-4

|  |  | Storage days |  |  |  |
|---|---|---|---|---|---|
|  |  | Initial | 1 | 2 | 7 |
| % ai | Clothianidin | 9.48 |  | 9.53 | 9.71 |
|  | Metconazole | 0.209 |  | 0.217 | 0.214 |
|  | Metalaxyl | 0.404 |  | 0.394 | 0.413 |
|  | pH | 7.7 | 7.7 | 7.8 | 7.5 |
| residue on 100 mesh sieve (%) |  | 0.003 |  |  | 0.000 |
| Median particle size (µm) |  | 1.09 | 1.24 | 1.54 | 1.38 |

The ready-to-use products thereby have about 9% of the formulation.

Applicants unexpectedly found that formulations of the present invention can be mixed with flowable concentrates for seed treatments several weeks prior to application without settlement of the active ingredients.

Comparative Example 4

Alternative Formulation of a Dispersible Concentrate

Applicants prepared another dispersible concentrate with the percentage of components as indicated below ("Formulation of Example 4").

TABLE 12

Formulation of Example 4

| Component | % w/w |
|---|---|
| Metconazole Technical | 2.30 |
| Metalaxyl Technical | 4.59 |
| GA 3 (gibberellic acid) | 0.005 |
| Hexylene Glycol | 40.57 |
| Celvol ®24-203 | 5.38 |
| Trimethylopropane | 1.47 |
| Terspserse ® 2500 | 1.47 |
| Terspserse ® 4894 | 0.23 |
| Agrimer ® VA6 | 2.96 |
| Surfynol ® 104PG | 0.17 |
| Legend MK ® | 0.17 |
| Water | To 100 |

Comparative Example 5

Alternative Formulation of a Dispersible Concentrate

Applicants prepared another dispersible concentrate with the percentage of components as indicated below ("Formulation of Example 5").

TABLE 13

Formulation of Example 5

| Component | % w/w |
|---|---|
| Metconazole Technical | 2.3 |
| Metalaxyl Technical | 4.5 |
| Hexylene Glycol | 5 |
| Pluronic ® P 104 | 0.75 |
| Aerosil ® R 792 | 1.0 |
| Propylene Glycol | 78.95 |
| Terspserse ® 2500 | 7.5 |

Example 6

Efficacy on Corn Seed in Illinois

Corn seeds were treated with 1 fluid ounce per one hundred weight (fl oz/cwt) or 65 mls/100 kg seed of the Formulations of Examples 1 and 4 prior to being planted in Illinois. Untreated seeds ("UTC") were planted to assess the disease impact in stand establishment. Besides the control, commercially available and known fungicides were applied to determine the effectiveness of formulations of the present invention. Maxim® XL (Maxim is a registered trademark of Syngenta) is a fungicide containing 21% fludioxonil and 8.4% mefenoxam in a proprietary formulation. Apron XL® (Apron XL is a registered trademark of Syngenta) is fungicide containing 33.3% of mefenoxam in a proprietary formulation. Metalaxyl was applied in a 30.1% formulation and metconazole was applied in an approximately 40% dispersion with approximately 4% glycerine and other inert ingredients.

At planting, the soil was inoculated with a fungus of the genus *Fusarium*, a common corn plant pathogen that causes stalk rot disease, to assess field performance and seedling protection of the above formulas.

"Plants per acre" was determined to establish stand density. "% disease" was calculated by observing number of plants with *Fusarium* infection. The "height (cm) on roots" was determined. The results of this field study are below in "Table 14. Stand Density and % Disease of Illinois Corn Plants after Seed Treatment."

TABLE 14

Stand Density and % Disease of Illinois Corn Plants Following Seed Treatments

| Formulation | Test Rates (fl oz/cwt) | Plants per acre 14DAP | 28DAP | % disease | Height (cm) on roots |
|---|---|---|---|---|---|
| UTC | N/A | 26789 | 27225 | 42.9 | 55.0 |
| Maxim ® + Apron ® XL | 0.08 + 0.085 | 25592 | 26463 | 26.6 | 58.8 |
| Metalaxyl | 0.15 | 25352 | 26049 | 18.0 | 61.0 |
| Metconazole | 0.052 | 28401 | 29011 | 37.6 | 57.3 |
| Form. of Ex. 4 | 1 | 28140 | 28662 | 15 | 59.3 |
| Form. of Ex. 1 | 1 | 27094 | 27791 | 8.6 | 60.8 |

Table 14 shows a significant increase in the stand density of corn plants 14 and 28 days after planting ("DAP") when the seeds were treated with the Formulation of Example 1 compared to the untreated control. Seeds treated with the Formulation of Example 1 led to a 3.98 fold reduction in the number of diseased plants. This is an unexpected result when compared to the commercially available fungicides.

Example 7

Efficacy on Corn Seed in Ohio

Corn seeds were treated with 1 fluid ounce per one hundred weight (fl oz/cwt) of the Formulations of Examples 1 and 4 prior to being planted in Ohio. Untreated seeds were planted to assess the disease impact in stand establishment. Besides the control, commercially available and known fungicides were applied to determine the effectiveness of formulations of the present invention.

At planting, the soil was inoculated with a fungus of the genus *Rhizoctonia*, a common corn plant pathogen that causes rot disease, to assess field performance and seedling protection of the above formulas.

"Plants per acre" was determined to establish stand density. The results of this field study are below in "Table 15. Stand Density of Ohio Corn Plants after Seed Treatment."

TABLE 15

Stand Density of Ohio Corn Plants Following Seed Treatments

| Formulation | Test Rates (fl oz/cwt) | Plants per acre 14DAP | 28DAP |
|---|---|---|---|
| UTC | N/A | 23538 | 27650 |
| Maxim ® + Apron ® XL | 0.08 + 0.085 | 27475 | 30538 |
| Metalaxyl | 0.15 | 22400 | 28700 |
| Metconazole | 0.052 | 28875 | 28700 |
| Form. of Ex. 1 | 1 | 27300 | 29663 |

Table 15 shows a significant increase in the stand density of corn plants 14 and 28 DAP when the seeds were treated with the Formulation of Example 1 compared to the untreated control.

Example 8

Efficacy on Corn Seed in Ontario

Corn seeds were treated with 1 fluid ounce per one hundred weight (fl oz/cwt) of the Formulations of Examples 1 and 4 and were planted in Ontario at two sites, as well as taken to yield. Untreated seeds were planted to assess the disease impact based on the reduction in number of plants caused by seed and seedling disease. At planting, the soil was inoculated with *Rhizoctonia* at Site 1 (ON1) and *Fusarium* at Site 2 (ON2). The results of the field trials are below in "Table 16. Stand Density (Plant Population per Acre) @ 19-28 Days after Planting of Corn Seed Receiving Seed Treatment."

TABLE 16

Stand Density (Plant Population per Acre) @ 19-28 Days after Planting of Corn Seed Receiving Seed Treatment

| Treatment | Site 1 (ON1) *Rhizoctonia*-Inoculated # plants | Site 2 (ON2) *Fusarium*-Inoculated # plants | Mean Stand Combined Trials # plants |
|---|---|---|---|
| Untreated | 16593 | 13760 | 15177 |
| Maxim 4FS + Apron XL @ .08 & .085 fl. oz./cwt. | 17807 | 24687 | 21247 |
| Form. of Ex. 4 @ 1 fl. oz./cwt. | 24282 | 19830 | 22056 |
| Form. of Ex. 1 @ 1 fl. oz./cwt. | 26306 | 20640 | 23473 |

Seeds treated with the Formulation of Example 1 across the two disease-inoculated trials resulted in greater than a 1.5 fold increase in the number of plants per acre over the untreated control and a 1.1 fold increase over the industry standard treatment.

TABLE 17

Yield (Bushel per Acre) of Corn Plants Receiving Seed Treatment

| Treatment | Site 1 (ON1) Rhizoctonia-Inoculated Bu/A | Site 2 (ON2) Fusarium-Inoculated Bu/A | Mean Stand Combined Trials Bu/A |
|---|---|---|---|
| Untreated | 116.0 | 41.6 | 78.8 |
| Maxim 4FS + Apron XL @ .08 & .085 fl. oz./cwt. | 113.0 | 63.9 | 88.5 |
| Form. of Ex. 4 @ 1 fl. oz./cwt. | 147.2 | 74.3 | 110.8 |
| Form. of Ex. 1 @ 1 fl. oz./cwt. | 165.0 | 80.3 | 122.7 |

Seeds treated with the Formulation of Example 1 gave a 1.56 fold increase in yield of corn over the untreated and a 1.39 fold increase over the industry standard.

An unexpected yield increase of the seeds treated with the Formulation of Example 1 in the *Fusarium*-inoculated trial was realized over the industry standard, as the initial plant population establishment of the Formulation of Example 1 was less in comparison.

Example 9

Efficacy on Corn Seeds in Mississippi

Corn seeds were treated with 1 fl oz/cwt of the Formulations of Examples 1 and 4 and were planted in Mississippi. Untreated seed was planted to assess the disease impact in emergence and final yield.

"% Emergence" was determined by counting the number of plants that emerged from the soil. Yield was determined by the number of bushels of corn that were produced in an acre "bu/A". The results of this field study can be seen below in "Table 18. Emergence Rate and Yield of Corn Plants after Seed Treatment."

TABLE 18

Emergence Rate and Yield of Corn Plants after Seed Treatment

| Formulation | Test Rates (fl oz/cwt) | % Emergence 20DAP | % Emergence 35DAP | Yield (bu/A) | Yield (kg/hectare) |
|---|---|---|---|---|---|
| UTC | N/A | 77 | 89 | 157.8 | 9900.1 |
| Maxim ® + Apron ® XL | 0.08 + 0.085 | 90.5 | 83.8 | 142.7 | 8953.3 |
| Metalaxyl | 0.15 | 91.5 | 83.3 | 154 | 9662.3 |
| Metconazole | 0.052 | 80.8 | 84.8 | 155.5 | 9756.4 |
| Form. of Ex. 4 | 1 | 80 | 82.5 | 143.9 | 9028.6 |
| Form. of Ex. 1 | 1 | 83.3 | 86.8 | 159.2 | 9988.5 |

Seeds treated with the Formulation of Example 1 unexpectedly resulted in a greater percentage of seeds emerging 35 DAP than either the Maxim® and Apron® XL combination, the metconazole formulation, or the metalaxyl formulation. Additionally, the Formulation of Example 1 had a greater final yield than any of the other treatments and control. These results prove the efficacy of the fungicide protection offered in the Formulation of Example 1.

Example 11

Safety of the Formulation of Example 1 to Wheat and Barley Seed

The Formulation of Example 1 was applied to wheat and barley seed using standard seed treatment slurry preparations and seed treatment equipment. The application rate was 1.0 fl. oz./cwt. seed. Initial germinations at time of treating and six months after treatment were monitored for seed safety of the formulation using standard warm and cold test germination methods. The results are portrayed below in the tables, indicating excellent seed safety of The Formulation of Example 1 to the treated seed over time, under normal and stress germination conditions.

TABLE 19

Wheat Germination Study:
2 Varieties (Gore and Madsen); Zero Time and 6 Months Germination

| | Gore Variety | | | | Madsen Variety | | | |
|---|---|---|---|---|---|---|---|---|
| | Warm | | Cold | | Warm | | Cold | |
| Treatment | 0 MO | 6 MO | 0 MO | 6 MO | 0 MO | 6 MO | 0 MO | 6 MO |
| Untreated | 99 | 96 | 94 | 96 | 98 | 97 | 93 | 93 |
| Form. of Ex. 1 | 98 | 96 | 90 | 91 | 98 | 96 | 92 | 93 |

TABLE 20

Barley Germination Study:
2 Varieties (Baroness and Lacey); Zero Time and 6 Months Germination

| | Baroness | | | | Lacey | | | |
|---|---|---|---|---|---|---|---|---|
| | Warm | | Cold | | Warm | | Cold | |
| Treatment | 0 MO | 6 MO | 0 MO | 6 MO | 0 MO | 6 MO | 0 MO | 6 MO |
| Untreated | 97 | 99 | 99 | 100 | 94 | 98 | 97 | 98 |
| Form. of Ex. 1 | 89 | 99 | 100 | 100 | 92 | 99 | 100 | 99 |

Accordingly it was found that the Formulation of Example 1 is safe and non-phytotoxic to seeds.

What is claimed is:

1. A non-aqueous pesticidal dispersible concentrate formulation consisting of:
    a) from about 2 to about 10% of a pesticidal agent consisting of a mixture of metconazole and metalaxyl;
    b) from 19 to 21% of hexylene glycol;
    c) from 69 to 71% of propylene glycol;
    d) a hydrophobic silica; and
    e) a difunctional block copolymer with terminal primary hydroxyl groups,
    wherein the weight percentages are based on the total weight of the formulation.

2. The pesticidal formulation of claim 1 wherein the hydrophobic silica is a fumed hydrophobic silica after treatment with hexamethyl disilazane.

3. A non-aqueous pesticidal dispersible concentrate formulation consisting of:
    a) from about 6 to about 8% of a pesticidal agent consisting of a mixture of metconazole and metalaxyl;
    b) from 19 to 21% of hexylene glycol;
    c) from 69 to 71% of propylene glycol;
    d) from about 1 to about 2% of hydrophobic silica; and
    e) from about 1 to about 2% of a difunctional block copolymer with terminal primary hydroxyl groups,
    wherein the weight percentages are based on the total weight of the formulation.

4. The pesticidal formulation of claim 3 wherein:
    a) the pesticidal agent consisting of a mixture of metconazole and metalaxyl is at a concentration from about 6 to about 7%;

b) the fumed hydrophobic silica that has been treated with hexamethyl disilazane is at a concentration from about 1 to about 2%, wherein the weight percentages are based on the total weight of the formulation.

5. The pesticidal formulation of claim 4 wherein:
a) metconazole is at a concentration from about 2 to about 3%; and
b) metalaxyl is at a concentration from about 4 to about 5%.

6. The pesticidal formulation of claim 5 wherein:
a) metconazole is at a concentration of about 2.3%;
b) metalaxyl is at a concentration of about 4.5%;
c) hexylene glycol is at a concentration of about 20%;
d) propylene glycol is at a concentration of about 70.1%;
e) fumed hydrophobic silica that has been treated with hexamethyl disilazane is at a concentration of about 1.5%; and
d) difunctional block copolymer surfactant with terminal primary hydroxyl groups is at a concentration of about 1.5%.

7. A ready-to-use product prepared from the formulation of claim 1 consists of:
a) a pesticidal agent consisting of a mixture of metconazole and metalaxyl at a concentration from about 0.5 to about 5%;
b) hexylene glycol at a concentration from about 1 to about 16%;
c) propylene glycol at a concentration from about 5 to about 55%;
d) hydrophobic silica at a concentration from about 0.1 to about 1.2%;
e) the difunctional block copolymer with terminal primary hydroxyl groups at a concentration from about 0.1 to about 10%; and
f) water at a concentration from about 5 to about 99%,
wherein the weight percentages are based on the total weight of the formulation.

8. A method of protecting plants comprising treating plant propagation material with a fungicidally effective amount of the ready-to-use product of according to claim 7.

9. A method of protecting plant propagation material from pests comprising applying to the plant propagation material an effective amount of the formulation of claim 1.

* * * * *